United States Patent [19]

Monthony et al.

[11] 4,254,096

[45] Mar. 3, 1981

[54] REAGENT COMBINATION FOR SOLID PHASE IMMUNOFLUORESCENT ASSAY

[75] Inventors: James F. Monthony, Albany; Michael W. Burgett, Half Moon Bay; Robert V. Dahlstrom, San Rafael, all of Calif.

[73] Assignee: Bio-Rad Laboratories, Inc., Richmond, Calif.

[21] Appl. No.: 81,741

[22] Filed: Oct. 4, 1979

Related U.S. Application Data

[60] Division of Ser. No. 875,475, Feb. 6, 1978, Pat. No. 4,201,763, which is a continuation of Ser. No. 621,197, Oct. 9, 1975, abandoned.

[51] Int. Cl.³ .................. G01N 33/52; G01N 33/54
[52] U.S. Cl. .................................. 424/8; 23/230 B; 424/7; 424/11; 424/12; 424/13; 424/78
[58] Field of Search ............... 424/7, 8, 11, 12, 13, 424/78; 23/230 B

[56] References Cited

U.S. PATENT DOCUMENTS

| | | | |
|---|---|---|---|
| 3,555,143 | 1/1971 | Axen | 424/12 X |
| 3,641,235 | 2/1972 | Weiss | 424/8 |
| 3,720,760 | 3/1973 | Bennick | 424/8 X |
| 3,853,987 | 12/1974 | Dreyer | 424/8 X |
| 3,901,654 | 8/1975 | Gross | 424/1 X |
| 3,925,018 | 12/1975 | Saunders | 23/230 B |
| 3,998,943 | 12/1976 | Ullman | 424/12 |

OTHER PUBLICATIONS

Molday, Nature, vol. 249, May 3, 1974, pp. 81–83.
Capel, J. Immunol. Methods, vol. 5, 1974, pp. 165–178.

*Primary Examiner*—Anna P. Fagelson
*Attorney, Agent, or Firm*—Townsend and Townsend

[57] ABSTRACT

An assay method suitable for antigens (or haptens) including proteins and polypeptides utilizing antibodies for the unknown protein or polypeptide in which the antibodies are covalently bound to water insoluble hydrophilic polymeric particles. Appropriate fluorescently labeled immune reactants are introduced during the method and together with the unknown antigen are immunologically bound, directly or indirectly, to the particles for separation from the reaction liquid. The particles have a size of about 0.1–10 microns and can be resuspended for direct measurement of the fluorescent labels in a fluorometer from which the unknown can be determined.

6 Claims, 2 Drawing Figures

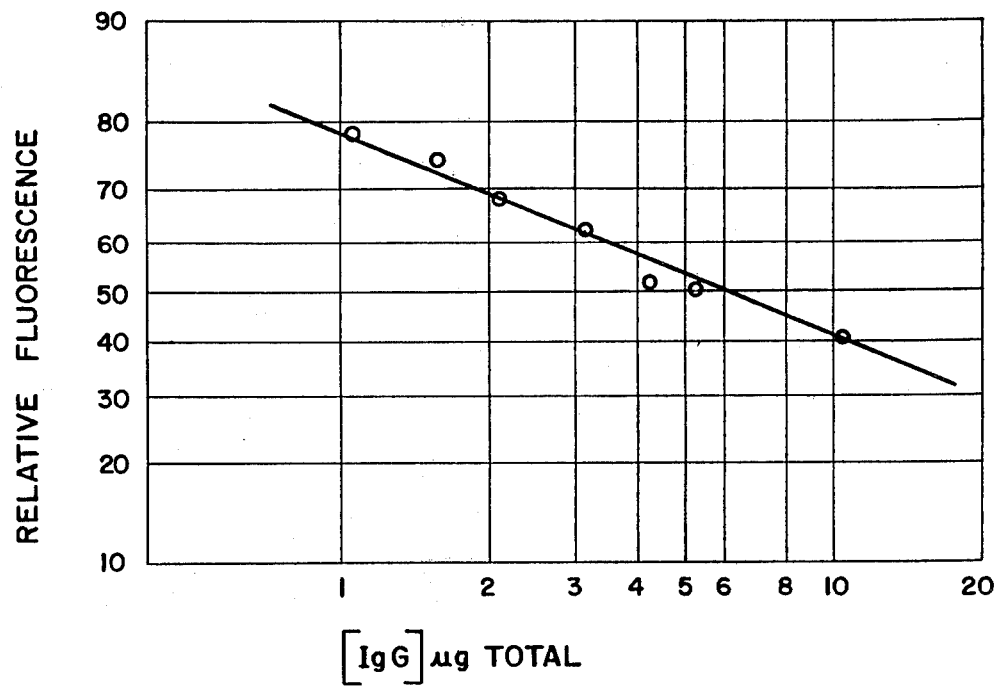
FIG_1
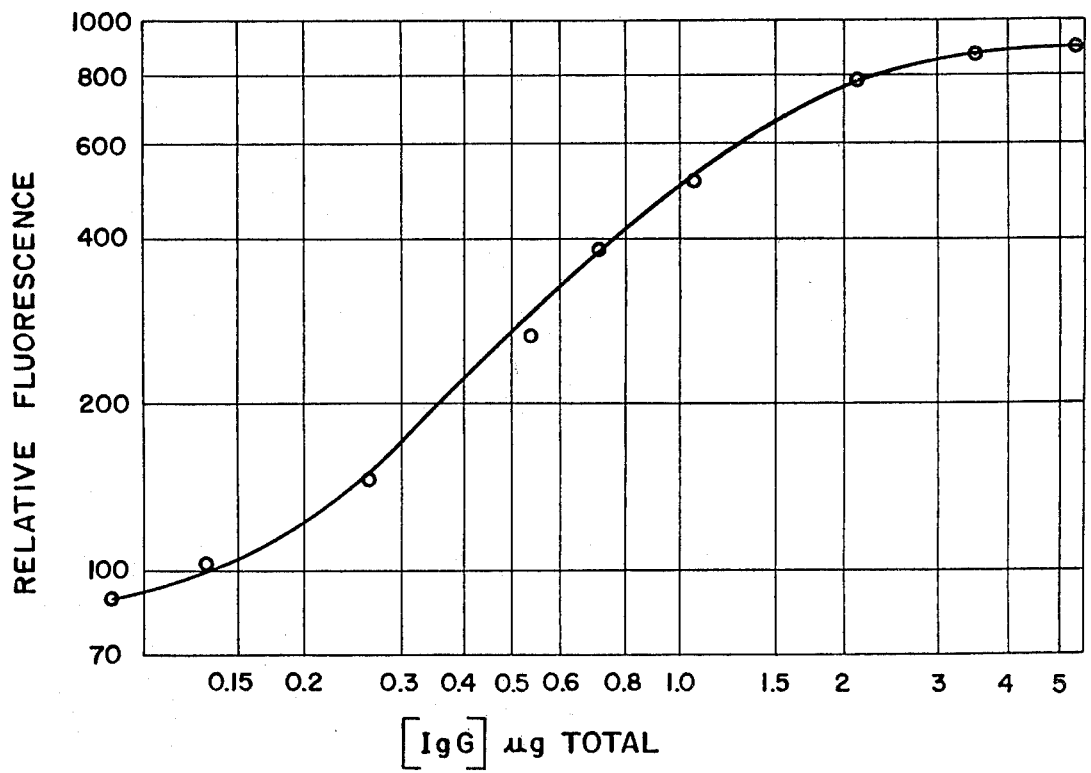
FIG_2

REAGENT COMBINATION FOR SOLID PHASE IMMUNOFLUORESCENT ASSAY

This is a division of application Ser. No. 875,475, filed Feb. 6, 1978 now U.S. Pat. No. 4,201,763 which in turn is a continuation of application Ser. No. 621,197, filed Oct. 9, 1975, now abandoned.

This invention relates to a method for the immunofluorescent assay of antigens (or haptens) and their antibodies. More particularly, it relates to the use of an immune reactant related to the antibody or anitgen (or hapten) to be determined which is covalently bonded or coupled to polymeric particles whose size permit direct measurement of a labeled immunological reagent's fluorescence in an aqueous suspension thereof.

The covalent coupling of antigens (or haptens) and antibodies to water insoluble polymers is well documented. Typical reports on this topic are:

Campbell, D. H., Leusher, E., and Lerman, L. S., Proc. Nat. Acad. U.S. 37, 575 (1951)

Weliky, N. and Weetall, H. H., Immunochemistry 2, 293 (1965)

Campbell, D. H. and Weliky, N., Methods in Immunology and Immunochemistry, Editors: Williams C. A. and Chase, M. W. Vol. 1, Academic Press, N.Y. (1967)

The technique has been used to detect various constituents and is the subject of several patents. In U.S. Pat. No. 3,555,143 issued Jan. 12, 1971 to R.E.A.V. Axen, et al., the patentees covalently bound antibodies to water insoluble polymers, mixed them with radioactive protein and unlabeled protein in a competitive binding technique.

In U.S. Pat. No. 3,867,517 issued Feb. 18, 1975 the patentee Chung-Mei Ling coated a test apparatus with hepatitis associated antibody or antigen, then contacted the apparatus with a solution containing the antigen or antibody. Thereafter this was exposed to hepatitis antigen or antibody labeled with radioactive isotope $I^{125}$ to give a sandwich. After washing, the amount of isotope attached could be quantitated.

Molday, et al (Molday, R. S., Dreyer, W. J., Rembaum, A. and Yen, S. P. S., Nature 249, May 2, 1974) and (The Journal of Cell Biology, Vol. 64, 75–88, 1975) report on the synthesis of latex spheres equal to or less than 1300 A in diameter, the fluorescent or radioactive tagging of the spheres, and the covalent bonding of antibodies to the spheres. These were subsequently used to locate antigens on cell surfaces.

Inman & Dintzis (Inman, J. K. and Dintzis, H. M., Biochemistry 8 (10) 4074–4082, 1969) described the chemical modification of polyacrylamide beads to introduce a wide variety of functional groups. The chemically reactive bead derivatives were used to covalently link antibodies or enzymes.

Ohno and Stahmann (Ohno, Y. and Stahmann, M. A., Immunochemistry 9, 1087–1093, 1972) subsequently determined that beads of about 10 microns in size, to which penicillin had been attached, gave better agglutination reactions than red blood cells when used in detecting antibodies to penicillin.

Immunochemical labeling techniques have been reviewed in Methods in Immunology and Immunochemistry, Editors: Williams, C. A. and Chase, M. W., Vol. 1, Acad. Press, N.Y. (1967) and Vol. III (1971).

The use of fluorescently labeled antibodies has been reviewed by Coons (Coons, A. H., Fluorescent Antibody Methods, J. F. Danielli (Editors) General Cytochemical Methods, Vol. 1, Academic Press, N.Y. 1958) and has found widespread use in the detection of microbial and tissue antigens by fluorescent microscopy.

Coons, et al (Weller, T. H. and Coons, A. H.) Proc. Soc. Exptl. Biol. Med. 86, 789 (1954) also described a method of determining cell bound antigen using a specific antibody plus a fluorescent anti-gamma globulin antibody. The same authors (Coons, A. H., Leduc, E. H. and Connolly, J. M., J. Exptl. Med. 102, 49, 1955) described a technique for determining cell bound antibody by using specific antigen plus specific fluorescent antibody.

Capel (Capel, P. J. A., J. of Immunological Methods 5, 165–178, 1974) coupled antibodies or antigens to the surface of agarose beads of a size ranging from 40–190μ. In this work he had to adjust conditions to prevent the antigen from penetrating the pores of the bead or the ensuing antigen-antibody reaction would be hindered. In his work he attached human IgG to agarose beads, reacted them with rabbit anti-human IgG antibody and then fluorescein isothiocyanate (FITC) labeled horse anti-rabbit Ig serum. He measured the amount of fluorescence attached by visualization with fluorescent microscopy. If antigen was to be measured, the anti-human IgG antibody was attached to the agarose beads, reacted with human IgG and FITC labeled horse anti-human Ig serum added and the fluorescence determined by fluorescent microscopy.

By way of summary, in the application of covalently coupled immune reactants with insoluble polymers to assays, immune reactants labeled with either radioactive tracers or fluorescent compounds have been employed. Radioactive tracers have the disadvantages of limited life and special handling requirements, as well as requiring expensive detection instrumentation. With respect to the prior use of fluorescent tracers, applications that might be considered an assay have been limited to indirect or relatively tedious and time consuming procedures such as measuring fluorescence of individual particles by visualization with fluorescent microscopy.

The method of the present invention permits measurement of fluorescently labeled particles by direct optical spectroscopy. The key to the method is in the selection of polymeric particle sizes which provide a substantially homogeneous suspension during execution of the assay. It has been discovered that such a condition exists upon which direct fluorometric measurements can be made where the polymeric particles have a size of about 0.1–10 microns and preferably where the particles have a size distribution within this range centered about 5 microns.

Utilizing such particles, an appropriate immune reactant immunlogically related to unknown antigen (or hapten) or antibody to be determined is covalently bonded thereto. The particles, unknown immune reactant, and appropriate fluorescently labelled immune reactant are mixed under conditions so that a quantity of the labelled immune reactant proportional to the concentration of the unknown immune reactant is immunologically bound, directly or indirectly, to the particles. The particles can then be readily physically separated and their fluorescence directly measured by fluorometry.

As used herein, "immunologically related" means that the immune reactant is either the same as the immune reactant being referred to or its homolog. An antibody is the "immunological homolog" of an antigen which produced it and vice versa. In the methods of this invention antigens and haptens perform entirely analogous functions. This will be indicated by referring to them as alternatives throughout.

More particularly, the present invention provides an improved immunofluorencence assay which comprises providing a plurality of water insoluble hydrophilic polymeric particles of about 0.1–10 microns in size and having covalently bonded thereto the immunological homolog for an antigen (or hapten) or antibody to be determined. The particles are combined with the antigen (or hapten) or antibody to be determined in aqueous solution to form an immunological bond therebetween. A fluorescently labeled antigen (or hapten) or antibody corresponding to the antigen (or hapten) or antibody to be determined is immunologically bound to said particles. The particles are separated from the aqueous solution and their fluorescence measured in an aqueous suspension by fluorometry to obtain information from which unknown antigen (or hapten) or antibody can be determined.

The method is especially suited for determining antigens (or haptens) selected from proteins and polypeptides utilizing antibodies against the protein or polypeptide. These antibodies are covalently bound to suitable water insoluble polymeric particles. Thus, in a preferred embodiment the improved assay comprises providing a plurality of water insoluble hydrophylic polymeric particles of about 0.1–10 microns in size and having covalently bonded thereto antibody for unknown antigen (or hapten) to be determined. Unknown antigen (or hapten) is immunologically bound to said particles in aqueous solution. In addition, fluorescently labeled immune reactant is combined to immunologically bind a portion thereof either directly or indirectly (through bound antigen or hapten) to said particles so that the bound labels are separable with said particles. The particles are separated from unbound immune reactant and the fluorescence of a fluid suspension is measured in a fluorometer to obtain information for the assay of unknown antigen (or hapten).

Any suitable water insoluble polymeric particle may be utilized. Generally the particle will be in spherical or bead form and will be selected from polymers which can be derivatized to give a terminal primary amine, terminal carboxyl, or hydrazide group. The antibody or antigen (or hapten) is then immobilized on the particle under conventional reaction conditions to produce a covalent bond therebetween. Preferred polymeric particles are formed from cross-linked polyacrylamides. Immobilization of immune reactants on such preferred substrates are reported by Inman & Dintzis as cited above. Other suitable polymeric particles include those reported in U.S. Pat. No. 3,555,143 in particular, as well as the other references above cited.

In carrying out the present assay method, a number of alternative techniques are available. The choice will usually be made depending upon the nature of the particular antigen (or hapten) or antibody to be determined and their availability. In general one of the following sequences will provide the most satisfactory option:

Sandwich Technique

The immobilized antibody (covalently attached to the polymeric particle, preferably in spherical or bead form) is reacted in an appropriate solution with specific bivalent or multivalent antigen (or hapten) in such concentrations that there is always an excess of antibody. After the reaction has gone to completion, fluorescently labeled antibody specific to the antigen (or hapten) is added in slight excess. Since the antigen (or hapten) has two or more sites for reaction and only one is occupied, the second labeled antibody will react with the unoccupied antigen (or hapten) site(s). The antibody beads, combined with the antigen (or hapten) and labeled antibody, are separated and measured in a fluorometer. The concentration of the antigen (or hapten) is directly related to the amount of fluorescence attached to the beads.

Sequential Saturation

Another approach is to react an excess of the immobilized antibody with the antigen (or hapten) in question. After the reaction has occurred, labeled antigen (or hapten) can be added which will occupy the available sites remaining on the antibody. The immobilized antibody-antigen (or hapten) complex can be separated and the label measured. The amount of labeled antigen (or hapten) immobilized will be inversely related to the amount of antigen (or hapten) in the sample. This approach may be necessary in the case of monovalent antigens (or haptens).

Antigen Excess

When antigen (or hapten) is in excess a competitive binding technique may be employed. Antibody specific for an antigen (or hapten) is attached to the particles. The amount of bound or solid phase antibody added to the system is sufficient to bind a limited amount of antigen (or hapten). The specific antigen (or hapten) in question and homologous labeled antigen (or hapten) are added to the antibody. Since the number of binding sites on the immobilized antibody is limited, the labeled and unlabeled antigens (or haptens) will compete for the sites. The amount of labeled antigen (or hapten) bound will be inversely related to the concentration of unlabeled antigen (or hapten) in the system and can be used as a means of quantitation of the unlabeled antigen (or hapten) in the system.

This technique can be combined with a second antibody technique. By the correct selection of an antibody fraction, the solid phase antibody can be used as a second antibody in the analyses, for example, of haptens that have only one combining site with antibodies. In this procedure, antibodies to a hapten, such as thyroxine, dinitrophenol or a steroid are prepared by well known procedures. The hapten is conjugated with the protein of one species and injected into a noncompatible species. That is, the hapten can be conjugated to human serum albumin and injected into rabbits. The rabbit will produce antibodies against the protein-hapten conjugate.

In this procedure, a second antibody is required and second antibodies are produced against, for example, a fraction of rabbit globulins by injecting them into a goat. This produces goat anti-rabbit antibodies. These can be conjugated to small polyacrylamide beads, for example, and used as a second antibody for any system in which the first antibody was produced in rabbits. Any series of animals may be used as long as antibodies against the first species are produced in a noncompatible second species.

In this procedure, the antibody-hapten or antigen combination does not differ significantly from unreacted antibody to allow convenient separation or precipitation. A second particle bound antibody, to the globulin fraction of the animal used to produce the first antibody, is utilized to cause precipitation to occur. In this case, the initially competitively bound antigen-first antibody combination may be considered the immunological homolog of the particle bound second antibody.

In another technique, hapten protein conjugates are used in a manner analogous to that described above for preparing antibodies to haptens. The antibodies to the hapten are covalently linked to the polyacrylamide beads to be used as a reagent for the determination of a hapten. Then the same hapten protein conjugate is prepared and the protein fluorescently labelled. This is used in a competitive binding assay or sequential saturation assay with the native hapten to be assayed. The technique provides an amplified molar fluorescent response.

Another variation of the technique is to covalently bind the antigen to the bead. The antigen bound to the bead is placed in competition with native antigen for limited amount of homologous antibody. The beads are separated and reacted with an excess of a fluorescently labelled second antibody directed against the antigen-antibody complex. The beads can be separated and the fluorescence measured. The amount of fluorescence is inversely related to the serum concentration of antigen to be measured.

The present invention contemplates the use of any suitable fluorescent compound in combination with antigens (or haptens) or antibodies as a label. The following are typical example of suitable compounds, together with references pertaining to their use as labels.

1. Fluorescein isothiocyanate
    The T. H. and feltkamp, T. E. W., Immunology, 18, 865 (1970)
2. Rhodamine B isothiocyanate
    Chen, R. F., Arch, Biochem, Biophys. 133, 263 (1969)
3. DNS chloride (5-dimethylamino-1-naphthalene sulfonylchloride)
    Weber, G., Biochem. J., 51, 155 (1952)
4. NBD chloride (7-chloro-4-nitro-benzo-2-oxa-1,3,-diazole)
    Ghosh, P. B. and Whitehouse, M. W., Biochem, J., 108, 155 (1968)
5. MDPF (2-methoxy-2,4-diphenyl-3(2H)-furanone)
    Weigele, M., DeBernardo, S., Leimgruber, W., Cleeland, R. and Grunberg, E., Biochem. Biophys. Res. Comm. 54, 899 (1973)
6. Fluorescamine (Fluram TM -Roche Diagnostics)
    Bohlen, P., Stein, S., Dairman, W. and Udenfriend, S., Arch. Biochem. Biophys. 155, 213 (1973)
7. O-Phthalaldehyde
    Benson, J. R. and Hare, P. E., Proc. Nat. Acad. Sci. (USA) 72, 619 (1975)
8. ANS (8-anilinonaphthalene-1-sulfonate)
    Hartman, B. K. and Udenfriend, S., Anal. Biochem. 30, 391 (1969)

TYPICAL GENERAL PROCEDURES

I. PREPARATION OF ANTIBODY BEADS

A. Derivatized polyacrylamide beads, having a functional capacity of 0.25 meq/g to 6 meq/g, are used for antibody attachment. (These may be obtained from Bio-Rad Laboratories of Richmond, Calif., as Affi-Gel 701, 702, 703 or derivative thereof.)

In addition, polyacrylamide beads, with an exclusion limit of 6–7,000 daltons, may be hydrolyzed by treatment with 2 M NaOH for 18 hours at 40° C. The beads are neutralized with HCl and washed with deionized water. The carboxyl capacity of the beads is measured by direct titration and preferably should be about 6 meq/g dry weight.

B. Carboxylate beads are suspended in 0.003 M phosphate buffer, pH 6.3, to a final concentration of 10 mg beads/ml.

C. A globulin fraction of an antiserum, specific for the antigen under test, is added to the beads at a concentration of 12 μg antibody/mg of beads. The reaction mixture is adjusted to pH 6.3.

D. A water soluble carbodiimide such as 1-ethyl-3(3-dimethylaminopropyl) carbodiimide (EDAC) is added at a concentration of 0.25 meq EDAC/meq of functional capacity of the bead. The reaction is maintained at pH 6.3 for one hour by the addition of dilute acid and/or base. After the first hour, the pH usually remains constant and the reaction is allowed to proceed over night at 4° C.

E. The coupled beads are washed twice with PBS (physiologically buffered saline, 0.15 M NaCl-0.01 M phosphate buffer, pH 7.2), three times with 5 M guanidine HCl in 0.05 M phosphate buffer, pH 7.5, two more times with PBS and finally twice with 0.005 M phosphate buffer, pH 7.5. The volume of the washes was about 50 ml/100 mg beads. The washes are carried out at 4° C. for maximal antibody activity.

F. The beads may be stored in 0.005 M phosphate buffer containing 0.01% sodium azide at 4° C.

II. ANTIGEN EXCESS ASSAY (Competitive Binding Assay)

A. Aliguots of 200 μl of a 10 mg/ml antibody bead suspension (~2 mg antibody beads) are added to a 13×100 mm borosilicate test tube containing 1.1 ml of PBS. The beads are pelleted by centrifugation (~8,000 g for ~1 min.)

B. The reaction is started by the addition of 10 μl labeled antigen (containing 10 mg antigen/ml), a sample of serum (10 μl of whole serum should fall in the range of the assay for 1 gG) and enough PBS to bring the assay mix to 1.5 ml. The mixture is shaken with a vortex mixer and incubated for 30 minutes at room temperature.

C. At 30 minutes, 4 ml of PBS is added to the assay mix. The sample is mixed and then centrifuged as above. The supernatant fluid is carefully discarded and the pellet is resuspended in 5 ml PBS. After about 10 minutes the suspension is recentrifuged and the supernatant fluid is again discarded.

D. The amount of labeled antigen on the beads is directly determined in a fluorometer. The quantity of labeled antigen picked up by the test sample is divided by the quantity picked up by a control sample (antibody beads plus labeled antigen with no serum) and plotted as a function of the concentration of antigen in mg/ml on log logit paper.

III. SANDWICH ASSAY

A. Aliquotes of 200 μl of a 10 mg/ml antibody bead suspension (~2 mg antibody beads) are added to a 13×100 mm borosilicate test tube containing 1.2 ml of PBS. The beads are pelleted by centrifugation (~8,000 g for ~1 min.)

B. A dilution of the serum is made (~1:1000 for IgG, ~1:100 for IgM and IgA). A 100 μl aliquot of the dilution is added to the tube from (A). The sample is mixed with a vortex mixer and allowed to incubate at room temperature for 3 hours.

C. A 100 ul aliquot of labeled antibody which should contain 20–50 μg antibody is added to the tube from (B) and the mixture is incubated an additional 30 minutes.

D. At 30 minutes, 4 ml of PBS is added to the assay mix. The sample is mixed and then centrifuged as above. The supernatant fluid is carefully discarded and the pellet is resuspended in 5 ml PBS. After about 10 min. the suspension is recentrifuged and the supernatant fluid is again discarded.

E. The relative fluorescence of labeled antibody on the bead is determined and this value is plotted versus the concentration of antigen is μg on log-log paper.

The following examples of specific embodiments will illustrate the invention in connection with rabbit anti-human IgG (RαHIgG) coupled to cross-linked polyacrylaminde beads.

EXAMPLE 1

A gram sample of terpolymer microbeads (less than 10 microns in diameter) was hydrolyzed by treatment with 2 M NaOH for 18 hours at 40° C. The beads were neutralized with HCl and washed six times with DI (de-ionized) $H_2O$.

A 500 mg sample of the above hydrolyzed beads was suspended in 100 ml 0.003 M phosphate buffer, pH 6.3. A 2 ml aliquot of an IgG fraction of rabbit anti-human IgG serum (Miles, Lot 14, Code 64-155) contained 2.9 mg/ml antibody in a 1% protein solution. The pH of the reaction mixture was adjusted to 6.3. An aliquot of 130 mg of EDAC (Bio-Rad) was added and the pH of the mixture was maintained at 6.3 with the addition of dilute acid and base for one hour. The reaction was allowed to proceed overnight with stirring at 4° C. The beads were washed twice with ~100 ml PBS, three times with 100 ml of 5 M guanidine HCl containing 0.01 M phosphate buffer, pH 7.5, and twice more with 100 ml PBS. After three hours at 4° C. the beads were washed twice with 100 ml of 0.005 M phosphate buffer, pH 7.5, and then suspended and stored in 50 ml of the last buffer containing 0.01% sodium azide (final concentration, 10 mg beads/ml).

EXAMPLE 2

Antigen Excess Assay

A 200 μl (2 mg) aliquot of RαHIgG beads from Example 1 was added to 1200 μl of PBS in a series of 1.5 ml Eppendorf centrifuge tubes. The beads were pelleted in an Eppendorf centrifuge Model 3200/30 by centrifugation at maximum speed for 1 minute (~12,000 g). A 10 μl aliquot of FITC labeled Human IgG (Cappel), various dilutions of Normal Human serum and enough PBS to bring the assay mix to 1.5 ml was added to each sample. The reaction was initiated by resuspending the beads with a vortex mixer. After 30 minutes the beads were centrifuged as above and the supernatant fluid was decanted. The beads were washed by resuspension in 1.5 ml PBS followed by centrifugation as above. The supernatant fluid was again poured off. This process was repeated once and the beads were resuspended in 5 ml 0.005 M Tris HCl, pH 8.5. The fluorescence of the beads was determined using a Turner Filter Fluorometer with filter 47B for the excitation light and filter 2A12 for the emission light.

The fluorescence of a tube containing a ~2 mg suspension of untreated beads is subtracted from the fluorescence of each test sample. The fluorescence of the test sample is then divided by the fluorescence of the control beads (Ab beads + fluorescent antigen with no serum added) and plotted versus concentration of antigen in mg on log-logit paper as shown in FIG. 1.

EXAMPLE 3

Sandwich Assay

The following components were mixed in a Eppendorf centrifuge tube and incubated for 18 hours at room temperature. 200 μl of RαHIgG beads from Example 1, 1,200 μl of PBS containing 1% BSA and 100 μl of a normal human serum dilution. At 18 hours the beads were centrifuged down in an Eppendorf Model 3200/30 at maximum speed for one minute (~12,000 g) and the supernatant fluid was decanted off. The beads were washed by resuspension in 1.5 ml PBS and centrifuged as above. The supernatant fluid was decanted off and the beads were resuspended in 1 ml of PBS containing 1% BSA. A 10 μl aliquot of FITC conjugated RαHIgG (Miles Lot 19, Code 64-169) was added to the beads and they were allowed to react at room temperature. After 30 minutes the beads were centrifuged and washed twice with PBS as above. The beads were resuspended in 5 ml 0.005 M Tris HCl, pH 8.5. The fluorescence of the beads was determined with a Turner filter fluorometer using a 47B filter for the excitation light and a 2A12 filter for the emission light. The fluorescence of the test sample less the fluorescence of a blank sample (a sample containing bead which had not been exposed to serum but was reacted with fluorescent antibody) was plotted versus IgG concentration in μg on log-log paper as shown in FIG. 2.

We claim:

1. An immunological reagent combination for use in an immunofluorescent assay comprising:
   (a) a plurality of water insoluble hydrophilic polymeric particles of about 0.1–10 microns in size which form a substantially homogeneous aqueous suspension and having covalently bonded thereto an immune reactant immunologically related to an unknown immune reactant to be determined; and
   (b) fluorescently labeled immune reactant immunologically related to said unknown,
   said particles and said fluorescently labeled immune reactant being in relative proportion for optimally carrying out an assay method comprising the steps of providing a plurality of water insoluble hydrophilic polymeric particles of about 0.1–10 microns in size which form a substantially homogeneous aqueous suspension and having covalently bonded thereto an immune reactant to be determined, providing a sample of unknown immune reactant to be determined, providing an appropriate amount of fluorescently labeled immune reactant immunologically related to said unknown, reacting said particles, sample, and labeled immune reactant to immunologically bind said particles in aqueous solution with a quantity of said labeled immune reactant proportional to the concentration of said unknown, physically separating all of said particles from said aqueous solution thereby separating the particles from unbound labeled immune reactant remaining in the aqueous solution, and measuring the fluorescence of an aqueous suspension of said separated particles by fluorometry, the fluorescence of labeled immune reactant bound to said particles being quantitatively related to the concentration of said unknown immune reactant.

2. The reagent combination acording to claim 1 wherein said particle-bound immune reactant is in molar excess of said fluorescently labeled immune reactant.

3. The reagent combination acording to claim 1 wherein said fluorescently labeled immune reactant is in molar excess of particle-bound immune reactant.

4. The reagent combination according to claim 1 wherein said particles are formed from a polymer selected from cross-linked polyacrylamide and derivatives thereof.

5. The reagent combination according to claim 1 wherein said fluorescently labeled immune reactant is labeled with fluorescein isothiocyanate.

6. The reagent combination according to claim 1 wherein said particles comprise a plurality of sizes with the size distribution centered around about 5 microns.

* * * * *